United States Patent [19]

Burkhardt et al.

[11] 4,289,895

[45] Sep. 15, 1981

[54] METHOD FOR THE PREPARATION OF OLIGOMERIC ALKYLENE TEREPHTHALATES

[75] Inventors: Rudolf Burkhardt, Troisdorf; Günther Meyer, Troisdorf-Sieglar; Reinhard Schmidt, Witten; Klaus Thewalt, Witten-Bommern, all of Fed. Rep. of Germany

[73] Assignee: Dynamit Nobel Aktiengesellschaft, Troisdorf, Fed. Rep. of Germany

[21] Appl. No.: 65,823

[22] Filed: Aug. 13, 1979

Related U.S. Application Data

[63] Continuation of Ser. No. 871,661, Jan. 23, 1978, abandoned, which is a continuation of Ser. No. 653,183, Jan. 28, 1976, abandoned.

[30] Foreign Application Priority Data

Feb. 1, 1975 [DE] Fed. Rep. of Germany ...... 2504258

[51] Int. Cl.³ .............................................. C07C 69/82
[52] U.S. Cl. ..................................... 560/92; 422/134; 528/309
[58] Field of Search ........................................ 560/92

[56] References Cited

U.S. PATENT DOCUMENTS

| | | | |
|---|---|---|---|
| 3,245,762 | 4/1966 | Ullrich et al. | 560/92 |
| 3,385,881 | 5/1968 | Bachmann et al. | 560/92 |
| 3,507,905 | 4/1970 | Gerantet et al. | 560/92 |
| 4,066,627 | 1/1978 | Borman | 560/92 |

*Primary Examiner*—Natalie Trousof
*Assistant Examiner*—Vera C. Clarke

[57] ABSTRACT

Oligomeric alkylene terephthalates having an average degree of condensation of 4 to 7 are produced by passing dimethylterephthalate and diol having at least 3 carbon atoms downwardly through a series of reaction chambers, each outfitted with stirring and heating means employed so that the temperature increases from stage to stage. Thereby transeterification is effected. The chambers are interconnected so that the methanol evolved in each chamber is vented without being admixed with the material undergoing transesterification in any of the other chambers. The transesterification product is then condensed at elevated temperature and under vacuum to produce the oligomer. The oligomers are high reactivity so that the further condensation thereof to polyesters is simplified.

13 Claims, 6 Drawing Figures

FIG. 2.
FIG. 3.
FIG. 4.
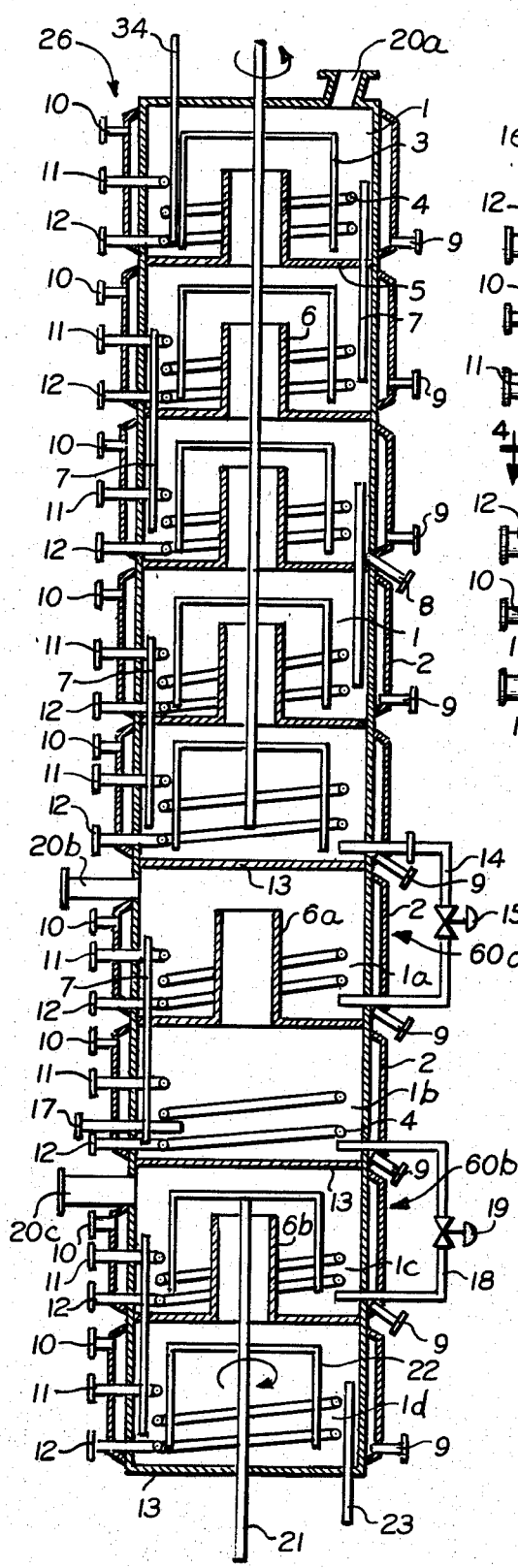
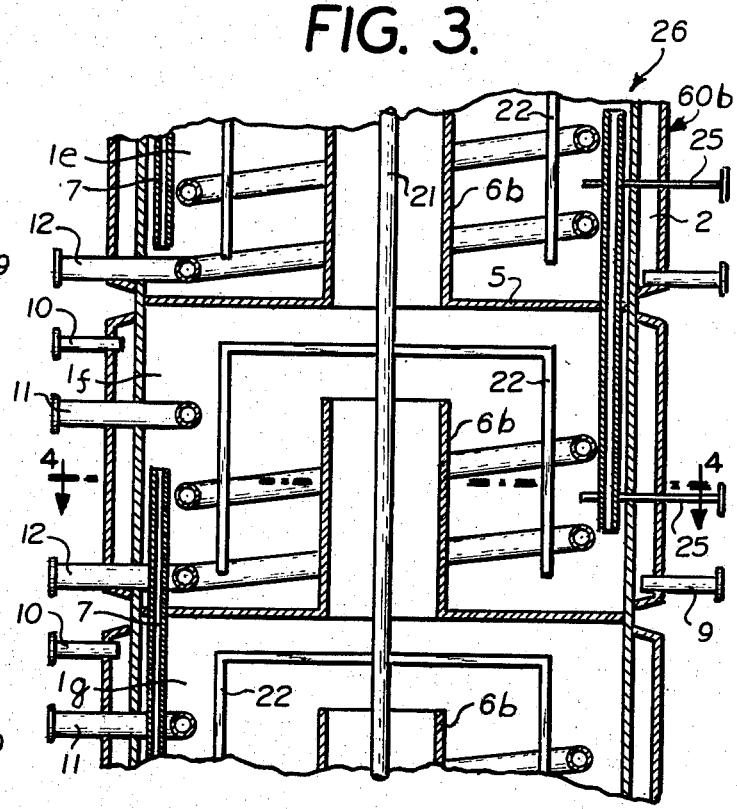
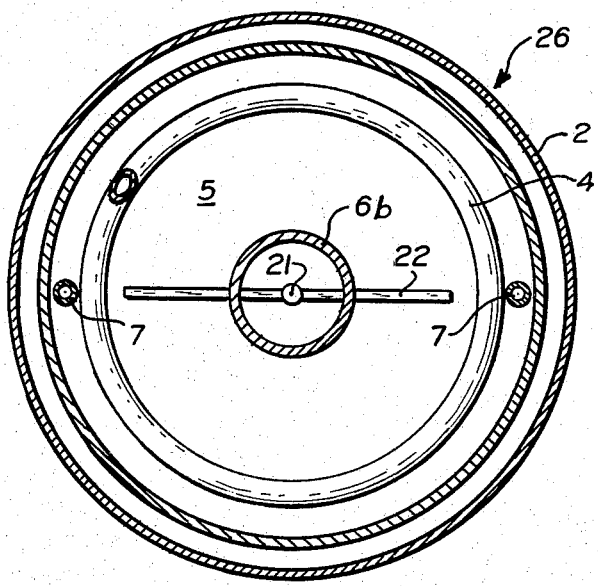

ent of the invention...

METHOD FOR THE PREPARATION OF OLIGOMERIC ALKYLENE TEREPHTHALATES

This is a continuation of application Ser. No. 871,661, filed Jan. 23, 1978, which is a continuation of Ser. No. 653,183, filed Jan. 28, 1976, both now abandoned.

BACKGROUND

The subject matter of the invention is a process for the production of oligomeric alkylene terephthalates having terminal hydroxyalkylene groups and degrees of condensation of 2 to 20, as well as an apparatus for the performance of this process.

The transesterification of benzene dicarboxylic acid esters with diols is an equilibrium reaction which can be shifted towards the monomeric bis-(hydroxyalkylene)-dicarboxylic acid ester by removing the methanol, and further on towards the polyester by the removal of excess diol.

Known processes operate in a discontinuous reaction, for example, in tanks provided with stirrers and other such reactors. The methanol that is released is separated in a superimposed or adjacent rectifying column, and then excess diol is removed in the same manner.

Such discontinuously prepared transesterification products do not fulfill all of the quality requirements in the further polycondensation.

A number of continuously operating apparatus shift the equilibrium of the transesterification reaction in the direction of the desired esters, by means of cascades of stirring tanks, in which case each cascade can have its own rectifying column, although all of the tanks in the cascade can be connected to a common rectifying column. These stirring tank cascades are expensive, they require an individual drive for each reactor and have a large heat radiating surface, and they require a large amount of space.

To avoid these disadvantages, upright columns with a variety of internal fixtures are used, and an additional column is superimposed on them or placed alongside them for the separation of methanol and diol.

For example, it has been proposed to transesterify DMT with ethylene glycol in bubble cap or screen baffle columns or in packed columns. The disadvantage in this case is that higher-boiling by-products that form remain in the sump product, and methanol and low-boiling by-products are given the opportunity to enter reverse reactions and secondary reactions. In German Auslegeschrift 1,593,309, the reaction mixture flows upwardly in a "flooded" column apparatus. By long contact, the vapors that form produce an incomplete transesterification by reverse reaction with methanol vapor.

German Offenlegungsschrift 1,920,954 describes a column divided by trays into 20 chambers in which the reaction mixture, by means of tangentially disposed drain tubes, sets the condensation mixture into rotation on the tray below. As the transformation increases, the reaction chambers are exposed to a pressure which diminishes step by step. In this case the necessary mixing action is no longer achieved due to the increased viscosity of the products.

By all of the above-named processes, polyesters of a high degree of condensation are prepared, but not oligomers.

THE INVENTION

It has now been found that the above-described disadvantages can be avoided in the continuous transesterification of benzene dicarboxylic acid esters with diols of three and more carbon atoms, in the presence of known transesterification catalysts, if at first oligomers are prepared separately, and if the process is performed at normal pressure or at a slightly elevated pressure in a column apparatus containing trays, wherein the reactants flow downwardly and are exposed to temperatures increasing continuously or step-wise in the direction of the reaction, the liquid level on the individual trays is kept low, the easily boiling alkanols forming in each stage of the reaction are removed from the column apparatus without flowing through the reaction mixture in the stage above, and the reactants are constantly stirred in all or most of the chambers, and then excess diol is removed in additional chambers in vacuo.

The catalyst is preferably delivered separately from the starting materials to the topmost tray, and additionally, if desired, to one or more of the trays below it, but it can also be delivered together with the starting materials.

It is desirable to dissolve the catalyst in the diol.

Suitable catalysts are, for example, alkyl titanates, such as tetrabutyltitanate, and in some cases zinc salts or manganese salts, especially acetates thereof.

Among the diols of three or more carbon atoms, 1,4-butanediol is preferred, although other diols can be used, such as 1,2-propanediol, 1,3-propanediol, hexanediols and octylene glycol. The diol can have up to 8 carbon atoms.

The diols are preferably free of solvents.

As the degree of transesterification progresses, the components are exposed to higher temperatures, so that the temperature ranges from 130° to 245° C., depending on the nature of the reactants and on the catalyst system, and preferably between 150° and 235° C. In general, the temperature at the beginning of the transesterification will be 130° to 160° C. in the topmost chamber, and will increase to from 180° to 210° C. in the bottommost chamber of the normal pressure stage.

The methanol respectively alkanol mixture in the transesterification and the volatile by-products, as well as a portion of the diol used for the transesterification corresponding to the conditions of temperature and pressure, can be removed from all chambers under normal pressure through a common, preferably central vapor chimney, while preventing them from mixing with the downwardly flowing reaction mixture, and they are delivered to a superimposed or adjacent rectifying unit for the separation of methanol, the recovery of diol and its separation from water and by-products such as, in some cases, tetrahydrofuran. The reaction part and the rectifying part of the apparatus has the same pressure, amounting from atmospheric pressure to a maximum of 4 bars and preferably to atmospheric pressure. The diol produced in the sump of the rectifier by the separation can be recycled directly to the upper chamber of the reaction part, and optionally also in portions to the following chambers.

In catalyst systems which favor the formation of by-products, or in which the formation of by-products is possible, provision is made for the maintenance of the molar ratio desired for, or favorable to, the reaction, by replacing the diol removed with the methanol with a like amount of fresh diol, which is introduced into the chambers.

The transesterification product which leaves the reaction part of the apparatus at normal or elevated pressure is fed through a regulating means which assures the desired detention time, into another part of the apparatus of the invention which operates at generally 180° to 250° C., preferably 220° to 240° C., and can also consist of at least one, preferably more chambers. The vacuum can best be increased in steps from chamber to chamber. Although the pressure is not limited to specific values and depends on the size and number of the chambers, it amounts in general to from 300 down to 20 Torr, preferably from 250 to 50 Torr.

These chambers, too, can be equipped with stirrers, preferably mounted on a common stirrer shaft. However, in one special embodiment of the apparatus of the invention, the vacuum chambers following the normal-pressure or elevated-pressure portion of the apparatus are not equipped with stirrers. This is possible because in this case the viscosity of the precondensate is low, and the diol excess remaining in the transesterification mixture is still great enough, and, in addition, a sufficient turbulence is assured for the rapid outgassing of the diol by the introduction of an inert gas.

If more than one or two vacuum chambers or stages are present, it is desirable to provide for stirring beginning with the third chamber.

The oligomers prepared by the process are products of superior purity, having a substantial and reliably high degree of transesterification, and having a $CH_3O$ content lower than 0.05 wt.-% and a free carboxyl group content of less than 30 m.eq.per kilogram.

The achievable reduced viscosity measured in a solution of 1 g per 100 ml in a 40:60 wt.-% mixture of tetrachlorethane and phenol at 25° C. is reproducible as well as variable within wide limits, and is generally less than 0.3, and preferably between 0.08 and 0.25. The content of monomeric terephthalic acid dialkanediol ester is in general low, amounting to from 0.5 to 20% by weight, although it can amount to as much as 30 wt.-%.

Surprisingly, the oligomers that are prepared are characterized by an especially high reactivity. They can be transformed by fusion condensation in the usual amount of time to a reduced viscosity of 0.8 to 0.9, and by solid phase condensation they can be transformed in half the usual time to polyalkyleneterephthalates of high molecular weight. The reactivity is so high that reduced viscosities, of over 2.0 to about 2.5 can easily be achieved, which cannot be achieved on a production scale by discontinuous processes. In the state of the art, for the achievement of polyesters of such high molecular weight in accordance with German Offenlegungsschrift No. 2,359,260, it was necessary to add from 0.5 to 3 moles of diaryl carbonates for each 100 moles of the polybutylene terephthalate first formed.

The claimed process furthermore results in highly reproducible characteristics and properties in the oligomers and in the polymers prepared therefrom by further condensation, as well as polyesters of high purity.

Additional subject matter of the invention, therefore, is the further processing of the oligomers to the end product polyester by further increasing the degree of condensation by means of molten phase reaction and solid phase condensation.

Such further condensation can be performed continuously or discontinuously by fusion condensation by known methods, generally at temperatures above 200° C. and ranging from 200° to 250° C., and in a vacuum of less than 1 mmHg, ranging generally from 0.1 to 0.25 mmHg and can then be continued, continuously or discontinuously, at generally lower temperatures (195°–215° C.) than in the preceding fusion condensation, and under the above-named vacuums or under an inert gas, as the case may be.

The heating can be performed by means of externally and/or internally mounted heating means.

The exhaust chimney common to these chambers is located preferably centrally on the vertical axis of the reactor, where the stirrer shaft is also located, the said stirrer shaft being preferably common to the chambers and being provided with stirrers, preferably for each chamber.

The depth on the trays amounts generally to 15 to 60 cm, preferably 25 to 30 cm, and overflow tubes pass through each chamber floor to carry the overflow into the chamber beneath.

Separately from the normal-pressure part of the apparatus, or preferably beneath it, additional heatable chambers of the vacuum part are provided, which can be equipped with exhaust gas chimneys common to several vacuum chambers and with stirrers on a common stirrer shaft, and also, if desired, with overflow tubes passing through the column trays or around the exterior.

Preferred, however, are two vacuum chambers without stirrers and with a common exhaust chimney, followed, if desired, by two or more additional vacuum chambers with stirrers and with an exhaust gas chimney common to them.

The apparatus is especially advantageous for performing the transesterification of DMT with diols, especially butanediol, and simutaneous and/or subsequent initial condensation of the transesterification mixture to oligomeric terephthalates, since tetrahydrofuran formed by cleavage of the butanediol is removed directly without further contact with the transesterification mixture, avoiding the formation of undesired by-products.

SUMMARY

Thus, the invention provides a process for production of oligomeric alkylene terephthalate having an average degree of condensation of 4 to 7, by transesterification of dimethylterephthalate and diol of at least three carbon atoms, and condensation of transesterification product. The process involves continuously passing the dimethylterephthalate, the diol, and a catalyst for the transesterification through a series of superposed reaction chambers from the uppermost serially to the lowermost chamber, for the transesterification. The proportion of dimethylterephthalate to diol introduced into the reaction chambers can be 1:1.1 to 1:1.5. The materials in the reaction chamber are heated so that the temperature increases stepwise from chamber to chamber, and the pressure is maintained at normal or above normal, in the reaction chambers. The transesterification product of the reaction chambers is passed through a vacuum zone maintained at a reduced pressure at a temperature for expelling of diol and production of the oligomer, and the oligomer is withdrawn from the vacuum zone.

Additional details on the apparatus of the invention will now be explained and represented in the drawing of examples of its embodiment.

FIG. 2 is a longitudinal cross section of a reactor consisting of a plurality of trays;

FIG. 3 represents one tray of the reactor with stirrer;

FIG. 4 is a section taken on line 4—4 in FIG. 3;

Figure 1:
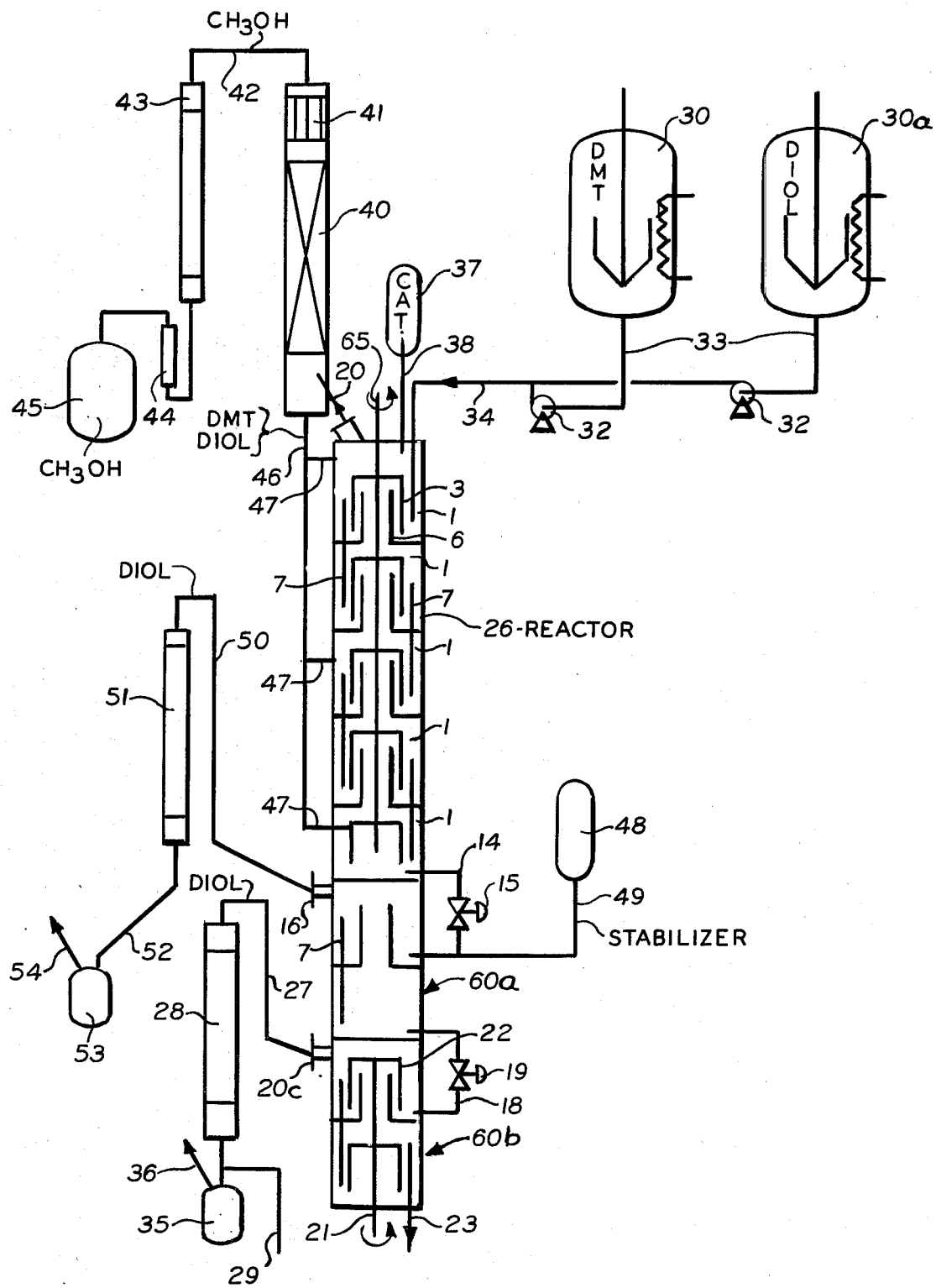
FIG. 1 is a schematic representation of an apparatus for the condensation of polyesters, which has a reactor consisting of a plurality of trays.

The apparatus represented in FIG. 1 for the preliminary condensation and condensation of polyesters shows the reactor 26. DMT and the diol are melted, or a mixture of both is heated. In FIG. 1, DMT and the diol are contained, respectively, in tanks 30 and 30a which are each outfitted with a stirrer and a heater. DMT and diol are delivered through suction lines 33 and discharge line 34 by the proportioning pumps 32 in a predetermined ratio to the vertically disposed and horizontally divided reactor 26. The heating system of the reactor has been omitted from FIG. 1 for the sake of simplicity; the heaters as well as other details are shown in FIG. 2. Catalyst is delivered through line 38 to the uppermost tray of the reactor from the reservoir 37 and a proportioning apparatus which is not illustrated. Under the influence of heat and the stirrers 3 fastened to a common shaft 65, methanol is liberated, which is delivered together with diol and DMT sublimate through the vapor line 20 to column 40 equipped with dephlegmator 41. Diol and DMT are recylcled through line 46 and can be delivered through branches 47 to various points in the reactor. Vaporous methanol is delivered through line 42 to the heat exchanger 43 where it is totally condensed, and is then fed through rate-of-flow meter 44 to the reservoir 45. The reaction mixture flows through connecting pipes 7 to the next tray below, where the reaction is continued at a higher temperature level. If desired, a stabilizer can be delivered from vessel 48 through line 49 by means of a proportioning apparatus which is not shown, to the uppermost tray, for example, of the trays of the reactors which are under a vacuum.

By applying a vacuum to the vacuum line 54, the diol is fed through vapor connections 16 and line 50 to the condenser 51, where it is condensed and delivered through line 52 into the receiver 53 and measured. To increase the degree of condensation, the oligomer mixture can be fed through level control 19 and line 18 to another part of the reactor where it is exposed to a higher vacuum and higher temperatures. The vapors of the diol are fed through connection 20c and line 27 to the condenser 28 where it is condensed and passes through line 29 which is collected in the measuring vessel 35. The vacuum is produced in line 36 by a pump which is not shown. Since the formation of diol vapors diminishes as the degree of condensation progresses, while the viscosity of the precondensate increases, a stirrer shaft 21 having stirrers 22 provided in this part of the reactor.

The reactor 26 is shown in detail in FIG. 2. It comprises a plurality of cylindrical chambers 1 with stirrers 3 and external heating jacket 2 with inlets 9 and outlets 10. The cylindrical sections are defined by the trays 5, above which internal coils 4 can be disposed, which are proveded with inlet and outlet connections 11 and 12, and which serve to increase the heating surface area.

The vaporous substances liberated are delivered through chimneys 6 directly to the vapor outlet 20a so as to avoid any exchange of substances with the reaction mixture. Sampling taps 8 can be provided at each tray.

The last, i.e. lowermost, tray 13 of the normal pressure part or of the elevated pressure part of the reactor is imperforate, i.e. it has no chimney. Through line 14 and level control 15, which is connected to maintain a constant level in the last tray of the reactor, the mixture or transesterification product and oligomers is passed into the vacuum section, which comprises two vacuum stages 60a and 60b. The first stage is provided by cylindrical chambers 1a and 1b similar in construction to cylindrical chamber 1 to the extent indicated by the reference characters. The bottom of the upper chamber 1a is provided with chimney 6a so that both chambers of stage 60a are vented directly to outlet 20b. The product of the first stage 60a is conveyed to the second stage 60b via line 18, which is outfitted with level control 19, which is connected to maintain a constant level in chamber 1b of the vacuum stage 60a. The second stage 60b is composed of cylindrical chambers 1c and 1d. Here also the bottom of upper section 1c is provided with a chimney 6b so that both chambers of stage 60b are vented directly to outlet 20c. Stage 60b is provided with stirrers 22 which are mounted on a common shaft 21.

In stage 60a of the reactor an agitator is not required due to the low viscosity and the turbulent evolution of gas. If necessary, the turbulence can by intensified by introducing inert gas through line 17.

In the stirrer-equipped stage 60b which follows next in some cases, the number of trays with stirrers 22 and common stirrer shaft 21 is governed by the desired degree of condensation.

The reaction product is taken from the reactor through pipe 23.

FIG. 3 is an enlarged scale and shows a vacuum stage 6b having three cylindrical chambers 1e, 1f, and 1g, each equipped with a chimney 6b and stirrer 22 mounted on a common shaft 21. Each tray is provided with a thermometer part 25.

EXAMPLES

EXAMPLE 1

27.8 parts of a mixture of dimethyl terephthalate and 1,4-butanediol in a molar ratio of 1:1.4, maintained at 140° C., were pumped per hour by means of a proportioning pump to the top tray of a column as is described above and having 5 trays or cylindrical chambers 1. Simutaneously, 0.2 parts per hour of a 9.8% solution of tetrabutyl titanate in 1,4-butanediol were metered in. The individual reaction trays were heated at 140° C. on the first tray to 185° C. on the bottom one—depending on the degree of transesterification—thereby allowing for the increasing melting point of the reaction mixture on the individual trays. During the reaction, 5.2 parts per hour of methanol were split off, with stirring. The product, which is transesterified to a degree of 95% and more, is continuously removed from the bottom tray of the stirring column in heated lines, and is let into the vacuum stages at 200° to 230° C. by means of regulating valves. At a vacuum of 240 Torr, 1.4 parts of excess 1,4-butanediol per hour, partially contaminated with THF, are distilled out and precipitated by a condenser that follows.

The oligomeric product is removed through alternately operated receivers and through a cooling roll.

The amount of product obtained is 21 parts per hour.

During the process, the degree of transesterification is determined in each stage. In the final stage a transformation of better than 99.6% is obtained in all cases. The oligomer has the following characteristics:

| | |
|---|---|
| Hydroxyl number | 100 (mol. wt. 1180) |
| Reduced viscosity | 0.14 [dl/g] |
| Carboxyl group content | 25 m.eq./kg |
| Avg. degree of condensation | 5 |
| CH$_3$O content | 0.038% by weight |

With this formulation and procedure a titanium content of less than 120 ppm is achieved, at a high reactivity. The polyester prepared from the oligomer corresponds to the physiologically unobjectionable formulation.

EXAMPLE 2

The amount of catalyst specified in Example 1 was increased to 0.4 parts of butyl titanate. At a comparable throughput per hour the following characteristics were obtained:

| | |
|---|---|
| Reduced viscosity | 0.14 [dl/g] |
| Avg. degree of condensation | 5 |
| CH$_3$O content | 0.030 wt. % |

EXAMPLE 3

Example 1 was repeated with a molar ratio of DMT to butanediol of 1:1.4; however, recovered butanediol obtained from the distillation in the vacuum stage during the transesterification was used. The reaction times and physical data were much the same as in Example 1:

| | |
|---|---|
| Reduced viscosity | 0.125 [dl/g] |
| $\bar{n}$ | 6 |
| CH$_3$O content | 0.035 wt. % |

EXAMPLE 4

(Further processing to the polyester)

The oligomer (OBT) prepared as in Example 1 with $\bar{n}=5$ was delivered under nitrogen at 245° C. to a discontinuous fusion condensation reactor. During the stirring at 15 rpm, with the immediate application of a vacuum of 0.2 mmHg, the butanediol liberated by the condensation was distilled off without foaming. After only 2.5 hours a reduced viscosity of 0.85 [dl/g] was achieved.

The polyester had a carboxyl group content of only 29 m.eq./kg in comparison to 44 m.eq./kg in the case of polyesters prepared from discontinuously produced transesterification products. It was taken from the reaction vessel and granulated by conventional methods.

Figure 5:
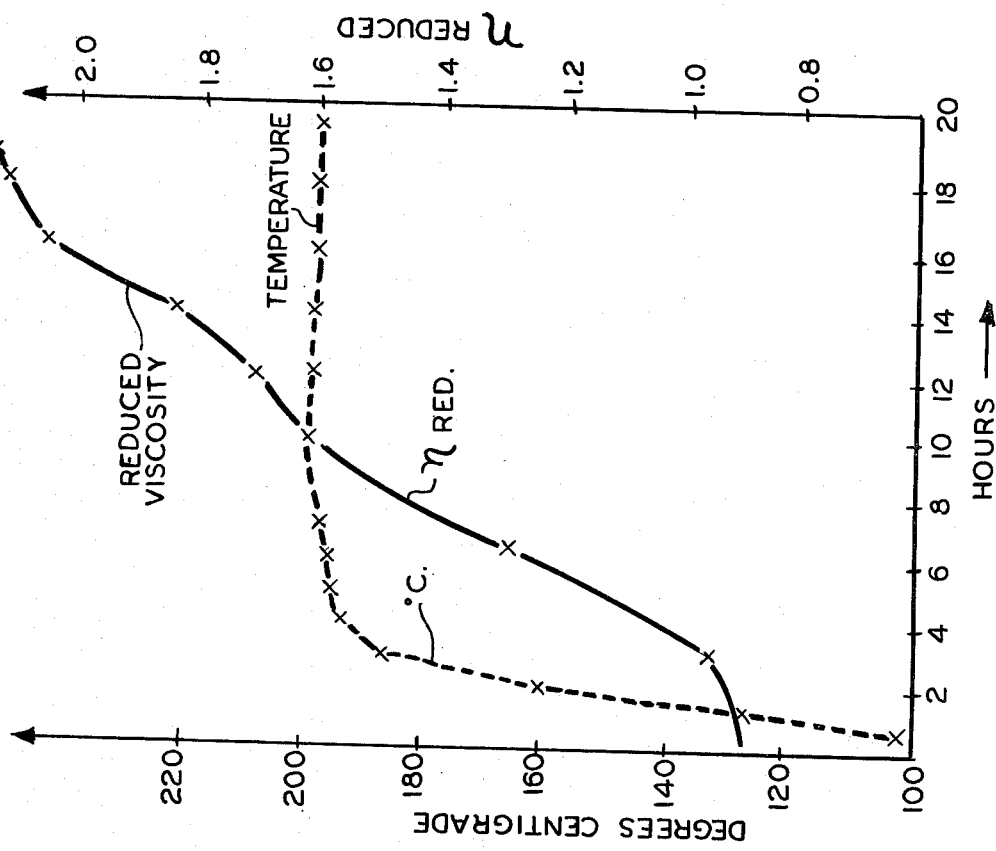

In a solid-phase condensation stage, the polyester granules obtained were heated in a vacuum of less than 1 Torr or under a current of inert gas, at 200° C. After only 6 hours a reduced viscosity of 1.6 was reached, and after 14 hours the reduced viscosity was 2.1 and the carboxyl group content was 11 m.eq./kg. In FIG. 5 there is shown the typical reduced viscosity curve of an OBT produced by this continuous process and fully condensed by molten phase and solid phase condensation. The viscosity increases steadily and almost linearly with the passage of time to high reduced viscosity values at only slight temperature fluctuations.

Figure 6:
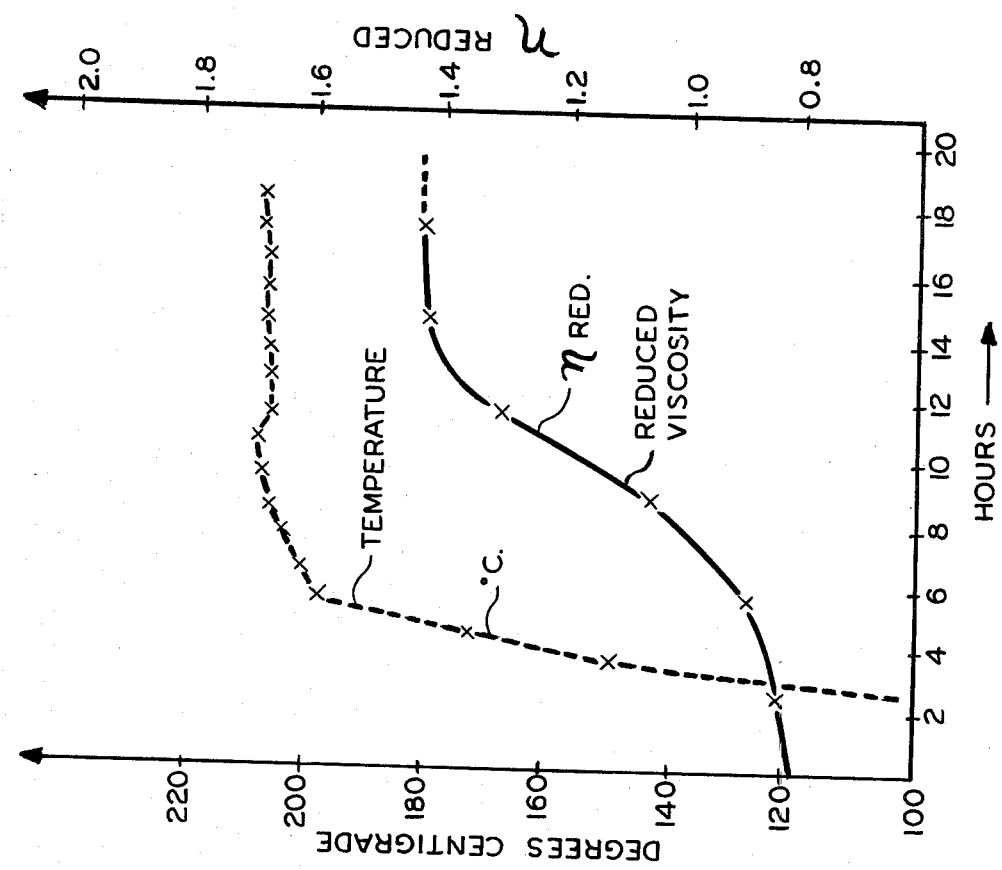
FIGS. 5 and 6 are graphic representations of the solid-phase condensation which shows the temperature and reduced viscosity of products in relation to the reaction time, and are further explained in Example 4.

In comparison thereto, a product produced discontinuously by the polytetramethylene terephthalate process and submitted to the solid phase condensation as described above, had after 6 hours, a reduced viscosity on only 1.15 dl/g and after 14 hours had attained a maximum of only 1.4 dl/g as shown in FIG. 6.

In FIG. 6 the solid line represents the measured values of reduced viscosity, whilst the dashed line is for the temperature of the granules.

EXAMPLE 5

(Further processing to polyester)

The polymer obtained in Example 2 is continuously fed to one or two screw reactors arranged in tandem and also continuously operating, and is brought to a reduced viscosity of 0.8 dl/g to 0.9 dl/g under a vacuum, with an average detention time of 2 hours (which is adapted to the detention time range of the transesterification reactor); it is pumped out by means of melt pumps and crushed in granulators. The polyester can be further condensed in a solid-phase reaction as in Example 4.

EXAMPLE 6

Same as Example 5, but with a detention time of 2.5 hours a reduced viscosity of 1.15 dl/g to 1.2 dl/g is reached, whereupon the product is taken out and granulated, and is further condensed in the same manner by solid-phase reaction. By the incorporation of 30% glass fibers, a material is obtained which has outstanding mechanical properties.

| | | | nach DIN-Nr. |
|---|---|---|---|
| Bending strength | 189.0 | N/mm$^2$ | 53 452 |
| Ultimate tensile strength | 146.6 | N/mm$^2$ | 53 455 |
| Elongation at rupture | 2 | % | 53 455 |
| Modulus of elasticity | 9500 | N/mm$^2$ | 53 457 |
| Notch impact toughness | | | |
| at 23° C. | 10.7 | kJ/m$^2$ | 53 453 |
| at 40° C. | 9.8 | kJ/m$^2$ | 53 453 |
| Martens number | 149.5-160 | °C. | |

By average degree of condensation is meant the average number of terephthalic acid groups per molecule.

Herein, with respect to pressure units, e.g. "a vacuum of less than 1 Torr" means an absolute pressure of less than 1 Torr, i.e. 1 mm of Hg.

The average degree of condensation can be 4 to 7, but the distribution may be 1 to 25.

The average degree of condensation is determined by analyzing the hydroxygroups and calculating the molecular-weight.

The range of the degree of condensation is determined after frationating of the oligomeric material by "gel permeation chromatography", determination of the hydroxyl numbers of the single fractions and claculation of the molecular-weights.

What is claimed is:

1. Process for production of oligomeric alkylene terephthalates having an average degree of condensation of 4 to 7, a CH$_3$O content of less than 0.05 wt.%, and a monomeric terephthalic acid dialkanediol ester content of up to 30 wt.%, by transesterification of dimethylterephthalate and diol of 3 to 8 carbon atoms and condensation of the transesterification product, which comprises:

(a) continuously passing the dimethylterephthalate, the diol, and a catalyst for the transesterification through a series of superposed reaction chambers from the uppermost chamber serially to the lowermost chamber, for the transesterification, in liquid phase, methanol being formed in the transesterification reaction and being distilled in the reaction chambers from the liquid phase during the transesterification, and withdrawing the methanol distilled from each chamber without intermixing thereof with the liquid present in any of the other chambers, (b) the molar proportion of dimethylterephthalate to diol introduced into the reaction chambers being 1:1.1 to 1:1.5, (c) heating said materials in the reaction chambers so that the temperature in the reaction chambers is in the range of 130°–245° C. and increases stepwise from chamber to chamber, and maintaining the pressure at normal or above normal in said reaction chambers, and stirring the materials during the reaction thereof with stirrers, (d) passing the transesterification product of the reaction chambers through a vacuum zone maintained at a reduced pressure of 20–300 Torr and temperature of 180°–250° C. for expelling of diol and production of said oligomer and withdrawing the oligmer from the vacuum zone, the temperature in the vacuum zone being higher than the highest temperature in the reaction chambers.

2. Process of claim 1, wherein the proportion of dimethylterephthalate to diol is 1:1.2 to 1:1.4, the pressure in said reaction chambers is normal pressure, and the oligomer is continuously withdrawn from the vacuum zone.

3. Process of claim 1, wherein the catalyst is introduced into the reaction chambers separately from the dimethylterephthalate and diol.

4. Process of claim 1, wherein the catalyst in solution in the diol is introduced into the reaction chambers.

5. Process of claim 1, wherein the catalyst is tetraalkyltitanate.

6. Process of claim 1, wherein the diol is 1,4-butanediol.

7. Process of claim 1, wherein the transesterification product is continuously introduced into the vacuum zone and the oligomerization is performed continuously.

8. Process of claim 1, wherein the oligomer is withdrawn as liquid from the vacuum zone and the liquid is cooled for solidification thereof.

9. Process of claim 1, wherein diol expelled in the vacuum zone is used in the transesterification reaction.

10. Process of claim 1, wherein the pressure in the reaction chambers is a maximum of 4 bars.

11. Process of claim 1, wherein the oligomeric alkylene terephthalate product has a free carboxyl group content of less than 30 m.eq. per kilogram.

12. Process of claim 1, wherein the content of monomeric terephthalic acid dialkanediol ester in the oligomer is 0.5 to 20 wt%.

13. Process of claim 1, wherein diol withdrawn from the reaction chambers is recovered and recycled to the reaction chambers.

* * * * *